US011324799B2

(12) United States Patent
Larsen et al.

(10) Patent No.: US 11,324,799 B2
(45) Date of Patent: May 10, 2022

(54) GAP JUNCTION INTERCELLULAR COMMUNICATION MODULATORS AND THEIR USE FOR THE TREATMENT OF DIABETIC EYE DISEASE

(71) Applicants: ZEALAND PHARMA A/S, Søborg (DK); BOSTON MEDICAL CENTER CORPORATION, Boston, MA (US)

(72) Inventors: Bjarne Due Larsen, Roskilde (DK); Ulrik Mouritzen, Rungsted Kyst (DK); Dongjoon Kim, Boston, MA (US); Sayon Roy, Boston, MA (US)

(73) Assignees: ZEALAND PHARMA A/S, Glostrup (DK); BOSTON MEDICAL CENTER CORPORATION, Boston, MA (US)

( * ) Notice: Subject to any disclaimer, the term of this patent is extended or adjusted under 35 U.S.C. 154(b) by 330 days.

(21) Appl. No.: 16/609,963

(22) PCT Filed: May 4, 2018

(86) PCT No.: PCT/EP2018/061537
§ 371 (c)(1),
(2) Date: Oct. 31, 2019

(87) PCT Pub. No.: WO2018/202865
PCT Pub. Date: Nov. 8, 2018

(65) Prior Publication Data
US 2020/0054602 A1 Feb. 20, 2020

Related U.S. Application Data

(60) Provisional application No. 62/502,322, filed on May 5, 2017.

(51) Int. Cl.
*A61K 38/08* (2019.01)
*A61P 3/10* (2006.01)
*A61K 31/40* (2006.01)

(52) U.S. Cl.
CPC .............. *A61K 38/08* (2013.01); *A61K 31/40* (2013.01); *A61P 3/10* (2018.01)

(58) Field of Classification Search
CPC .................................................. A61K 38/08
See application file for complete search history.

(56) References Cited

U.S. PATENT DOCUMENTS

| 4,775,743 | A | 10/1988 | Mimura et al. |
| 4,780,528 | A | 10/1988 | Takemoto et al. |
| 4,849,525 | A | 7/1989 | Weller, III et al. |
| 5,120,859 | A | 6/1992 | Webb |
| 5,707,991 | A | 1/1998 | Capet et al. |
| 6,046,306 | A | 4/2000 | Breipohl et al. |
| 6,399,629 | B1 | 6/2002 | Chamberland et al. |
| 7,622,496 | B2 | 11/2009 | Larsen et al. |
| 7,741,356 | B2 | 6/2010 | Breslin et al. |
| 8,026,272 | B2 | 9/2011 | Larsen et al. |
| 8,431,540 | B2 | 4/2013 | Larsen et al. |
| 8,927,590 | B2 | 1/2015 | Alimardanov et al. |
| 9,469,609 | B2 | 10/2016 | Alimardanov et al. |
| 2005/0203143 | A1 | 9/2005 | Breslin et al. |
| 2006/0183739 | A1 | 8/2006 | Tsaklakidis et al. |
| 2007/0149460 | A1 | 6/2007 | Larsen et al. |
| 2007/0232574 | A1 | 10/2007 | Galey et al. |
| 2008/0188545 | A1 | 8/2008 | Alimardanov et al. |
| 2010/0249207 | A1 | 9/2010 | Alimardanov et al. |

FOREIGN PATENT DOCUMENTS

| CN | 1528745 | A | 9/2004 |
| DE | 3831936 | A1 | 4/1989 |
| EP | 0052991 | A1 | 6/1982 |
| EP | 0071544 | A1 | 2/1983 |
| EP | 0088350 | A1 | 9/1983 |
| EP | 0132304 | A2 | 1/1985 |
| EP | 0175266 | A2 | 3/1986 |
| EP | 0254032 | A2 | 1/1988 |
| EP | 0566157 | A1 | 10/1993 |
| EP | 0672700 | A1 | 9/1995 |
| EP | 1604977 | A1 | 12/2005 |
| GB | 2159160 | A | 11/1985 |
| WO | WO 95/13069 | A1 | 5/1995 |
| WO | WO 95/30647 | A1 | 11/1995 |
| WO | WO 96/09820 | A1 | 4/1996 |
| WO | WO 97/36873 | A1 | 10/1997 |
| WO | WO 98/08815 | A1 | 3/1998 |
| WO | WO 98/10653 | A1 | 3/1998 |
| WO | WO 98/17679 | A1 | 4/1998 |
| WO | WO 98/25897 | A1 | 6/1998 |
| WO | WO 99/09991 | A1 | 3/1999 |
| WO | WO 00/23421 | A1 | 4/2000 |

(Continued)

OTHER PUBLICATIONS

Vippagunta et al. (2001).*
Aonuma et al., "Studies on Heart. XIX. Isolation of an Atrial Peptide that improves the Rhythmicity of Cultured Myocardial Cell Clusters", Chem. Pharm. Bull. , 1980, vol. 28, No. 11, pp. 3332-3339.
Barrette et al., "Connexin 43 (Cx43) Upregulation Protects Retinal Endothelial Cells Against High Glucose Insult", Jan. 28, 2013, URL: https://www.bumc.bu.edu/busm/files/2016/01/enrichment-poster-barrette-kevin.pdf, XP055493406.
Bobbie et al., "Reduced Connexin 43 Expression and Its Effect on the Development of Vascular Lesions in Retinas of Diabetic Mice", Investigative Ophthalmology & Visual Science, Jul. 2010, vol. 51, No. 7, pp. 3758-3763.

(Continued)

*Primary Examiner* — Paul V Ward
(74) *Attorney, Agent, or Firm* — Birch, Stewart, Kolasch & Birch, LLP (57) ABSTRACT

The use of gap junction intercellular communication (GJIC) modulators in the treatment or prevention of diabetic eye disease is disclosed, and more particularly to their use for the treatment or prevention of early stage diabetic retinopathy and diabetic macular edema by inhibiting apoptosis of retinal endothelial cells and inhibiting pericyte loss.

12 Claims, 8 Drawing Sheets

(56) References Cited

FOREIGN PATENT DOCUMENTS

| WO | WO 01/07436 A2 | 2/2001 |
|---|---|---|
| WO | WO 01/26644 A2 | 4/2001 |
| WO | WO 01/34594 A1 | 5/2001 |
| WO | WO 01/62775 A2 | 8/2001 |
| WO | WO 01/74796 A1 | 10/2001 |
| WO | WO 01/79162 A2 | 10/2001 |
| WO | WO 01/83517 A1 | 11/2001 |
| WO | WO 01/98344 A2 | 12/2001 |
| WO | WO 02/08244 A2 | 1/2002 |
| WO | WO 02/08251 A2 | 1/2002 |
| WO | WO 02/08256 A2 | 1/2002 |
| WO | WO 02/30421 A2 | 4/2002 |
| WO | WO 02/30462 A2 | 4/2002 |
| WO | WO 02/32869 A2 | 4/2002 |
| WO | WO 02/39976 A1 | 5/2002 |
| WO | WO 02/077017 A2 | 10/2002 |
| WO | WO 02/089738 A2 | 11/2002 |
| WO | WO 03/013571 A1 | 2/2003 |
| WO | WO 03/062228 A1 | 7/2003 |
| WO | WO 03/062265 A2 | 7/2003 |
| WO | WO 03/072528 A2 | 9/2003 |
| WO | WO 2004/005248 A1 | 1/2004 |
| WO | WO 2004/020599 A2 | 3/2004 |
| WO | WO 2004/045518 A2 | 6/2004 |
| WO | WO 2004/048400 A1 | 6/2004 |
| WO | WO 2004/087646 A2 | 10/2004 |
| WO | WO 2004/099134 A2 | 11/2004 |
| WO | WO 2005/037214 A2 | 4/2005 |
| WO | WO 2005/085197 A1 | 9/2005 |
| WO | WO 2005/095403 A2 | 10/2005 |
| WO | WO 2006/020276 A2 | 2/2006 |
| WO | WO 2006/114401 A2 | 11/2006 |
| WO | WO 2007/078990 A2 | 7/2007 |
| WO | WO 2008/058016 A2 | 5/2008 |
| WO | WO 2008/063323 A2 | 5/2008 |
| WO | WO 2008/079266 A2 | 7/2008 |
| WO | WO 2008/079412 A2 | 7/2008 |
| WO | WO 2009/010733 A1 | 1/2009 |
| WO | WO 2012/088425 A2 | 6/2012 |
| WO | WO 2012/125869 A1 | 9/2012 |
| WO | WO 2013/163423 A1 | 10/2013 |
| WO | WO 2015/017034 A1 | 2/2015 |
| WO | WO 2016/029191 A2 | 2/2016 |
| WO | WO 2017/009199 A1 | 1/2017 |

OTHER PUBLICATIONS

Butera et al., "Discovery of (2S,4R)-1-(2-Aminoacetyl)-4-benzamidopyrrolidine-2-carboxylic Acid Hydrochloride (GAP-134)[13], an Orally Active Small Molecule Gap-Junction Modifier for the Treatment of Atrial Fibrillation", 2009, J. Med. Chem., 2009, vol. 52, pp. 908-911.

Dhein et al., "A new synthetic antiarrhythmic peptide reduces dispersion of epicardial activation recovery interval and diminishes alterations of epicardial activation patterns induced by regional ischemia", Naunyn-Schmiedeberg's Arch Pharmacol, 1994, vol. 350, pp. 174-184.

Higuchi et al., "Pro-drugs as Novel Drug Delivery Systems", American Chemical Society: Washington, DC, 1975, A.C.S. Symposium Series, vol. 14, 6 pages.

International Search Report, issued in PCT/EP2018/061537, dated Jul. 27, 2018.

Kuwabara et al. "Studies of Retinal Vascular Patterns", Part I. Normal Architecture, Archives of Ophthalmology, 1960, vol. 64, pp. 904-911.

Liu et al., "Abstract 208: Rotigaptide Remodels Connexin 43 Expression in a Prolonged Ventricular-Fibrillation in Swine", Circulation, 2018, vol. 122:A208, 2 pages.

Michela et al., "Role of connexin 43 in cardiovascular diseases", European Journal of Pharmacology, 2015, vol. 768, pp. 71-76.

Müller et al., "Increase in gap junction conductance by an antiarrhythmic peptide", Eur. J. Pharmacol., 1997, vol. 327, pp. 65-72.

Muto et al., "High Glucose Alters Cx43 Expression and Gap Junction Intercellular Communication in Retinal Müller Cells: Promotes Müller Cell and Pericyte Apoptosis", Investigative Opthalmology & Visual Science, 2014, vol. 55, pp. 4327-4337.

Su et al., "Effects of rotigaptide (ZP123) on connexin43 remodeling in canine ventricular fibrillation", Molecular Medicine Reports, 2015, vol. 12, pp. 5746-5752.

Tien et al., "Association of reduced Connexin 43 expression with retinal vascular lesions in human diabetic retinopathy", Experimental Eye Research, 2015, vol. 146, pp. 103-106.

Written Opinion of the International Searching Authority, issued in PCT/EP2018/061537, dated Jul. 27, 2018.

Alzheimerstreatment.org, "Alzheimer's Disease Treatment Phases," Mar. 10, 2008, 3 pages.

Berrée et al., "N-Boc Ethyl Oxamate: A New Nitrogen Nucleophile for Use in Mitsunobu Reactions." Tetrahedron Letters, vol. 39, No. 45, 1998, pp. 8275-8276.

Bhagwat et al., "4-Substituted Proline Derivatives that Inhibit Angiotensin Converting Enzyme and Neutral Endopeptidase 24.11," Bioorganic & Medicinal Chemistry Letters, vol. 4, No. 22, 1994, pp. 2673-2676.

Bridges et al., "Conformationally Defined Neurotransmitter Analogues. Selective Inhibition of Glutamate Uptake by One Pyrrolidine-2,4-dicarboxylate Diastereomer," Journal of Medicinal Chemistry. vol. 34, No. 2. 1991, pp. 717-725.

Carmichael, "Rodent Models of Focal Stroke: Size, Mechanism, and Purpose," NeuroRx: The Journal of the American Society for Experimental NeuroTherapeutics, vol. 2, No. 3, Jul. 2005, pp. 396-409.

Consumer Reports, "Best Buy Drugs, Evaluating Prescrption Drugs Used to Treat: Alzheimer's Disease, Comparing Effectiveness, Safety and Price," Mar. 2006, pp. 1-16.

Database Registry, "Glycine, N-(3,5-diaminobenzoyl)," Database Accession No. 90559-49-2, Nov. 16, 1984, 1 page.

De Diego et al., "New Gly-Pro-Glu (GPE) Analogues: Expedite Solid-phase Synthesis and Biological Activity." Bioorganic & Medicinal Chemistry Letters, vol. 16, 2006 (Available online Nov. 29, 2005), pp. 1392-1396.

Gangamani et al., "Synthesis of N-(Purinyl/Pyrimidinyl acetyl)-4-Aminoproline Diastereomers with Potential Use in PNA Synthesis," Tetrahedron, vol. 52, No. 47, 1996, pp. 15017-15030.

Gregson et al., "Linker Length Madulates DNA Cross-Linking Reactivity and Cytotoxic Potency of C8/C8' Ether-Linked C2-exo-Unsaturated Pyrrolo[2,1-c][1,4]benzodiazepine (PBD) Dimers," Journal of Medicinal Chemistry, vol. 47, No. 5, 2004 (Published on Web Jan. 30, 2004), pp. 1161-1174.

Hennan et al., "GAP-134 ([2S,4R]-1-[2-Aminoacetyl]-4-Benzamidopyrolidine-2-Carboxylic Acid) Prevents Spontaneous Ventricular Arrhythmias and Reduces Infarct Size During Myocardial Ischema/Reperfusion Injury in Open-Chest Dogs," Journal of Cardiovascular Pharmacology Therapeutics, vol. 14, No. 3, Sep. 2009. pp. 207-214 (total 9 pages).

Khankari et al., "Pharmaceutical Hydrates," Thermochimica Acta, vol. 248, 1995, pp. 61-79.

Lemmens et al., "Genetics of Atrial Fibrillation and Possible Implications for Ischemic Stroke," Stroke Research and Treatment, vol. 2011, Article ID 208694, 2011, pp. 1-18.

Liu et al., "Abstract 208: Rotigaptide Remodels Connexin 43 Expression in a Prolonged Ventricular-Fibrillation in Swine," Resuscitation Science Symposium Session Title: Session VIII: Best Original Resuscitation Science, Circulation, vol. 122, Mar. 23, 2018 (Originally published), 2 pages.

Mayo Clinic, "Myocardial ischemia," http://www.mayoclinic.com/health/myocardial-ischemia/DS01179/DSECTON=prevention, Aug. 10, 2012, 2 pages.

Morady et al., "The Treatment of Atrial Fibrillation," University of Michigan Electrophysiology Service, Jul. 2009, pp. 1-12.

Neiss et al., "Antihypertensive Peplide Derivatives," Dalabase Accession No. 1986:479371 CAPLUS, 1986, 2 pages.

(56) References Cited

OTHER PUBLICATIONS

Petrillo et al., "Carboxyalkyl Amino Acid Derivatives of Various Substituted Prolines." Database Accession No. 1985:25039, CAPLUS, 1985, 2 pages.

Pfeifer et al., "Stabilisation of β-hairpin Conformations in a Protein Surface Mimetic Using a Bicyclic Template Derived from (2S,3R,4R)-diaminoproline," Chem. Commun., 1998, pp. 1977-1978.

Pfeifer et al., "Synthesis and Solution Conformation of β-Hairpin Mimetics Utilizing a Template Derived from (2S,3R,4R)-Diaminoproline," Helvetica Chimica Acta, vol. 83, 2000, pp. 444-464.

Su et al., "Effects of Rotigaptide (ZP123) on Connexin43 Remodeling in Canine Ventricular Fibrillation," Molecular Medicine Reports, vol. 12, 2015, pp. 5746-5752 (total 8 pages).

U.S. Office Action, dated May 9, 2008, for U.S. Appl. No. 11/643,192.

Watkins et al., "The Relationship between Physicochemical Properties, In Vitro Activity and Pharmacokinetic Profiles of Analogues of Diamine-Containing Efflux Pump Inhibitors," Bioorganic & Medicinal Chemistry Letters, vol. 13, No. 23, 2003, pp. 4241-4244.

Wikipedia, "Antiarrhythmic Agent," http://en.wikipedia.org/wiki/Antiarrhythmic_agent, Apr. 29, 2011, pp. 1-9.

Yelin et al., "Stereochemistry of the Reductive Amination of 4-Oxoproline Derivatives with Glycine Esters," Russian Journal of Bioorganic Chemistry, vol. 28, No. 6, 2002, pp. 444-449.

Engstrøm et al., "Danegaptide for primary percutaneous coronary intervention in acute myocardial infarction patients: a phase 2 randomised clinical trial," Heart, vol. 104, 2018 (published online Mar. 30, 2018), pp. 1593-1599.

Guo et al., "Connexin43 Mimetic Peptide Improves Retinal Function and Reduces Inflammation in a Light-Damaged Albino Rat Model," Invest Ophthalmol Vis Sci, vol. 57, No. 10, Aug. 2016, pp. 3961-3973.

Mugisho et al., "Immunohistochemical Characterization of Connexin43 Expression in a Mouse Model of Diabetic Retinopathy and in Human Donor Retinas," International Journal of Molecular Sciences, vol. 18, No. 2567, 2017, pp. 1-14.

* cited by examiner

FIG. 6

GAP JUNCTION INTERCELLULAR COMMUNICATION MODULATORS AND THEIR USE FOR THE TREATMENT OF DIABETIC EYE DISEASE

CROSS REFERENCE TO RELATED APPLICATIONS

This application is the National Phase of PCT International Application No. PCT/EP2018/061537, filed on May 4, 2018, which claims priority under 35 U.S.C. 119(e) to U.S. Provisional Application No. 62/502,322, filed on May 5, 2017, all of which are hereby expressly incorporated by reference into the present application.

FIELD OF THE INVENTION

The present invention relates to gap junction intercellular communication (GJIC) modulators and their use of the treatment or prevention of diabetic eye disease, and more particularly to their use for the treatment or prevention of diabetic retinopathy and diabetic macular edema. The present invention further relates to pharmaceutical compositions adapted for the delivery of gap junction intercellular communication modulators to the eye.

BACKGROUND OF THE INVENTION

There is increasing recognition that intercellular communication is essential for cellular homeostasis, proliferation and differentiation. Such communication is believed to be facilitated by gap junctions. These structures are thought to be a route for coupling cells and permitting "cross-talk". The cross-talk between gap junctions is referred to as "gap junctional intercellular communication" (GJIC). Generally, gap junctions are specialized regions of the cell membrane that contain clusters of hundreds to thousands of densely packed channels that directly connect the cytoplasm of two adjacent cells. The gap junction channels are composed of two hemichannels, or connexons, provided by each of two neighbouring cells. Each connexon, in turn, is made up of six proteins called connexins.

Diabetic retinopathy is the leading cause of vision loss and blindness among working-age adults. Retinal vascular cell loss is a characteristic hallmark of early diabetic retinopathy. It is known that accelerated retinal vascular cell loss is, at least in part, due to high glucose-induced apoptosis.

A particular problem with these conditions is that the early stages of diabetic retinopathy usually have limited or no symptoms. Thus, the disease often progresses unnoticed until it affects vision. Bleeding from abnormal retinal blood vessels can cause the appearance of "floating" spots. These spots sometimes clear on their own. This means that without prompt treatment, bleeding often recurs, increasing the risk of permanent vision loss. If diabetic macular edema (DME) occurs, it can cause blurred vision. A further problem is that vision lost to diabetic retinopathy may be irreversible.

Late stage diabetic retinopathy or DME can be treated with several therapies that may be used alone or in combination. Generally these therapies target the growth factors produced in late stage diabetic retinopathy. The therapies include anti-VEGF injection therapy in which anti-VEGF drugs are injected into the vitreous gel to block a protein called vascular endothelial growth factor (VEGF), which can stimulate abnormal blood vessels to grow and leak fluid. Blocking VEGF can slow down (brake) abnormal blood vessel growth and decrease fluid in the retina. Available anti-VEGF drugs include Avastin (bevacizumab), Lucentis (ranibizumab), and Eylea (aflibercept) and all three drugs are safe and effective for treating most people with DME. However, most patients require monthly anti-VEGF injections for the first six months of treatment. Thereafter, injections are needed less often: typically three to four during the second six months of treatment, about four during the second year of treatment, two in the third year, one in the fourth year, and none in the fifth year. Dilated eye exams may be needed less often as the disease stabilizes. However, all of these treatments need to be administered by an eye care professional and require administration by injection.

Accordingly, there is a need in the art for further treatments for diabetic eye disease, and especially early stage diabetic retinopathy and diabetic macular edema.

SUMMARY OF THE INVENTION

Broadly, the present invention relates compounds that are gap junction intercellular communication (GJIC) modulators for use in methods of treatment or prevention of diabetic eye disease, and in particular in the treatment or prevention of diabetic retinopathy and diabetic macular edema, typically in human patients. In some preferred aspects, the present invention is particularly concerned with the treatment or prevention of early stages diabetic retinopathy.

Although the role of gap junction intercellular communication (GJIC) has been extensively studied in various tissues, the present invention concerns its involvement with apoptotic cell death and pericyte migration in the diabetic retina. Gap junction channels allow the passage of ions, nutrients, and other signaling molecules (up to 1 kD) between neighboring cells. Importantly, connexin 43 (Cx43)-mediated GJIC plays a critical role in regulating cell growth, vascular tightness and cell death in the retina, and is thus an integral factor in maintaining retinal vascular homeostasis. Cx43 is abundantly expressed in the retina, which suggests a substantial amount of gap junction coupling. However, under high glucose and diabetic conditions, Cx43 expression is downregulated and its functionality is impaired, thereby compromising GJIC activity in retinal vascular cells. Moreover, high glucose- and diabetes-induced Cx43 downregulation and decreased GJIC activity plays a critical role in the increased vascular cell death in the retinas of diabetic mice, rats, and humans exhibiting a significant increase in the number of acellular capillaries and pericyte loss.

In the experiments described herein, we have shown that administration of a gap junction modulator, danegaptide (2S,4R)-1-(2-aminoacetyl)-4-benzoylamino-pyrrolidine-2-carboxylic acid (J. Med. Chem. 52(4): 908-911, 2009), prevents cell-cell GJ uncoupling under high glucose condition and prevents high glucose-induced apoptosis in retinal vascular cells. The experiments described herein further investigated whether these protective effects seen in vitro translate in an in vivo model of diabetes. In particular, the results disclosed in the present application investigated whether administration of danegaptide can prevent the development of acellular capillaries and pericyte loss in the retinas of diabetic rats. Three different in vitro systems were tested that informed on cell coupling, permeability as surrogate for vascular tightness/vascular leakage and apoptosis.

Moreover, it is known that blood vessels, including those present in the eye, are composed of two interacting cell types, see Song et al. Neuro-Oncology, July 2005, 453-464. Thus, endothelial cells form an inner lining of the vessel wall, while pericytes surround the surface of the vascular tube, supporting and maintaining vessel growth and help to inhibit leakage from the vessel. Pericytes are therefore functionally significant because when vessels lose pericytes, they become haemorrhagic and hyperdilated, leading to conditions such as edema, and diabetic retinopathy, and ultimately blindness. In addition to the effect of GJIC modulators on retinal endothelial cells, the present application shows that pericyte loss in a rat diabetic retinopathy model can be significantly decreased by administration of a GJIC modulator.

Furthermore, the efficacy of mode of delivery of danegaptide was determined in an intravitreal injection route and a systemic delivery route using an osmotic pump.

Accordingly, in a first aspect, the present invention provides a GJIC modulator compound as described herein for use in a method for the treatment or prevention of diabetic eye disease in a human subject, the method comprising administering to the subject a therapeutically effective amount of said GJIC modulator compound; or a pharmaceutically acceptable salt thereof.

Preferably, the GJIC modulator compound is selected from (2S,4R)-1-(2-aminoacetyl)-4-benzoylamino-pyrrolidine-2-carboxylic acid and Ac-DTyr-DPro-DHyp-Gly-DAla-Gly-NH$_2$; or a pharmaceutically acceptable salt or hydrate thereof.

Preferably, the GJIC modulator compounds are for use in the treatment or prevention of early diabetic retinopathy and diabetic macular edema. This is advantageous as many present forms of treatment of diabetic retinopathy are focused on the treatment of advanced stages of the disease, such as proliferative diabetic retinopathy (PDR), in which growth factors secreted by the retina trigger the proliferation of new blood vessels. Thus, the present invention provides an approach for the treatment or prevention of diabetic eye disease at a point before this advanced stage of the condition.

In a further aspect, the present invention provides pharmaceutical compositions adapted for the delivery of GJIC modulator compounds to the eye.

The GJIC modulator compounds described herein may enable cells to protect themselves during diabetic eye disease. Without wishing to be bound to any particular theory, the inventors speculate that the compounds may have stabilizing effects on the cells, reducing the tendency for mitochondria to become leaky and/or reducing the tendency for cells to develop a leaky outer cell membrane and/or improving the intercellular coupling of cells. The compounds may result in better coupling between cells, enabling the cells to share available energy (ATP) and enable intercellular signalling, including calcium signalling.

In a further aspect, the present invention provides the use of a compound selected from: (2S,4R)-1-(2-aminoacetyl)-4-benzoylamino-pyrrolidine-2-carboxylic acid; and Ac-DTyr-DPro-DHyp-Gly-DAla-Gly-NH$_2$; or a pharmaceutically acceptable salt or hydrate thereof, for the preparation of a medicament for the treatment or prevention of early stage diabetic eye disease or diabetic macular edema in a human subject, the method comprising administering to the subject a therapeutically effective amount of the compound, or a pharmaceutically acceptable salt thereof.

In a further aspect, the present invention provides a method of treating or preventing early stage diabetic eye disease or diabetic macular edema in a human subject, the method comprising administering to the human subject a therapeutically effective amount of the compound, or a pharmaceutically acceptable salt or hydrate thereof, wherein the compound is selected from: (2S,4R)-1-(2-aminoacetyl)-4-benzoylamino-pyrrolidine-2-carboxylic acid; and Ac-DTyr-DPro-DHyp-Gly-DAla-Gly-NH$_2$; or a pharmaceutically acceptable salt or hydrate thereof.

In a further aspect, the present invention provides a pharmaceutical composition comprising a GJIC modulator compound as described herein for use in a method as described herein, the pharmaceutical composition comprising said GJIC modulator compound and a pharmaceutically acceptable excipient. Preferably, the GJIC modulator is for administration in an eye drop formulation, via a contact lens, via a nasal spray or via injection, e.g. intravitreal injection. Systemic administration, e.g. through the use of tablets or capsules, is also possible.

Embodiments of the present invention will now be described by way of example and not limitation with reference to the accompanying figures. However, various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIG. 2. Effect of danegaptide (DG) on the development of AC and PL in diabetic rat retinas. Representative images showing retinal vascular networks from (A) WT, (B) DM, (C) DM+intravitreal injection (IV) of 1000 nM DG, (D) DM+IV of dH20, (E) DM+osmotic pump (OP) DG, and (F) DM+OP dH20 rats. AC (arrows); PL (open arrows). Graphical illustration showing cumulative RTD data demonstrates that the number of (G) AC and (H) PL is significantly increased in diabetic rat retinas compared to those of non-diabetic rat retinas. Importantly, intravitreally (IV) injection of danegaptide significantly reduced the number of AC and PL compared to IV injection of water as control in diabetic rat retinas. Moreover, systemic delivery of danegaptide via osmotic pumps (OP) significantly reduced the number of AC and PL compared to systemic delivery of water via OP in diabetic rat retinas. Improving cell-cell coupling prevented the development of AC and PL in the danegaptide treated retinas (**=p<0.001; *=p<0.01; n=6-9 animals per group).

FIG. 3. Effect of danegaptide (DG) on retinal vascular leakage. Graphical illustration showing cumulative IVP data demonstrates that retinal vascular leakage is significantly increased in diabetic rat retinas compared to those of non-diabetic rat retinas. Importantly, intravitreally (IV) injection of DG significantly reduced vascular leakage compared to IV injection of water as control in diabetic rat retinas. Moreover, systemic delivery of DG via osmotic pumps (OP) significantly reduced vascular leakage compared to systemic delivery of water via OP in diabetic rat retinas. Improving cell-cell coupling prevented diabetes-induced vascular leakage in the DG treated retinas. (**=p<0.001; n=8-10 animals per group).

FIG. 4. Effect of danegaptide (DG) on retinal vascular permeability. Representative images of the retinal whole mounts show capillary networks of (A) wild type (WT), (B) diabetic (DM), (C) DM+intravitreal injection (IV) of 1000 nM DG, (D) DM+IV of dH$_2$0, (E) DM+osmotic pump (OP) DG and (F) DM+OP dH$_2$O rats. Improving cell-cell coupling prevented diabetes-induced vascular leakage in the DG treated retinas. Scale bar=50 µm.

DETAILED DESCRIPTION

Definitions

Unless specified otherwise, the following definitions are provided for specific terms.

In the present description and claims the standard three-letter and one-letter codes for natural amino acids are used. The term "peptide" herein designates a chain of two or more amino acid moieties (amino acid residues) that are linked by means of a peptide bond. In general, peptides may contain one or more naturally occurring amino acids and/or one or more non-naturally occurring amino acids.

In the present context, the term "naturally occurring amino acid" refers to one of the following 20 amino acids: Ala (A), Cys (C), Ser (S), Thr (T), Asp (D), Glu (E), Asn (N), Gln (Q), His (H), Arg (R), Lys (K), Ile (I), Leu (L), Met (M), Val (V), Phe (F), Tyr (Y), Trp (W), Gly (G), and Pro (P). In naturally occurring peptide molecules these acids (with the exception of Gly, which lacks a chiral centre) generally occur in the form of L-amino acid residues, but compounds suitable for use in the present invention include peptides comprising D-amino acid residues (such as Ac-DTyr-DPro-DHyp-Gly-DAla-Gly-NH$_2$).

Amino acid three letter codes are as used in the art. Hyp refers to 4-hydroxyproline.

The compounds for use in the present invention may contain two or more asymmetric atoms (also referred to as chiral centers), giving rise to the possibility of the occurrence of diastereomers. Compounds suited for use in the present invention include such diastereomers.

As used herein, the term "vascular cells" includes endothelial cells and pericytes.

Diabetic Eye Disease

Diabetic eye disease are a group of eye conditions that affect people with diabetes. These conditions include diabetic retinopathy, diabetic macular edema (DME), cataract, and glaucoma. All forms of diabetic eye disease have the potential to cause severe vision loss and blindness and, as such, are a serious complication of diabetes.

Diabetic retinopathy involves changes to retinal blood vessels that can cause them to bleed or leak fluid, distorting vision. Diabetic retinopathy is the most common cause of vision loss among people with diabetes and a leading cause of blindness among working-age adults. DME is a consequence of diabetic retinopathy that causes swelling in the area of the retina called the macula.

Chronically high blood sugar from diabetes is associated with damage to the tiny blood vessels in the retina, leading to diabetic retinopathy. The retina detects light and converts it to signals sent through the optic nerve to the brain. Diabetic retinopathy can cause blood vessels in the retina to leak fluid or haemorrhage (bleed), distorting vision. In its most advanced stage, new abnormal blood vessels proliferate (increase in number) on the surface of the retina, which can lead to scarring and cell loss in the retina.

It is generally accepted that diabetic retinopathy progresses through four stages, see https://nei.nih.gov/health/diabetic/retinopathy:

1. Mild non-proliferative retinopathy. Small areas of balloon-like swelling in the retina's tiny blood vessels, called microaneurysms, occur at this earliest stage of the disease. These microaneurysms may leak fluid into the retina.

2. Moderate non-proliferative retinopathy. As the disease progresses, blood vessels that nourish the retina may swell and distort. They may also lose their ability to transport blood. Both conditions cause characteristic changes to the appearance of the retina and may contribute to DME.

3. Severe non-proliferative retinopathy. Many more blood vessels are blocked, depriving blood supply to areas of the retina. These areas secrete growth factors that signal the retina to grow new blood vessels.

4. Proliferative diabetic retinopathy (PDR). At this advanced stage, growth factors secreted by the retina trigger the proliferation of new blood vessels, which grow along the inside surface of the retina and into the vitreous gel, the fluid that fills the eye. The new blood vessels are fragile, which makes them more likely to leak and bleed. Accompanying scar tissue can contract and cause retinal detachment, the pulling away of the retina from underlying tissue, like wallpaper peeling away from a wall. Retinal detachment can lead to permanent vision loss.

As the present invention targets the role of gap junctions, in preferred aspects, the present invention is concerned with the treatment or prevention of patients with early stage diabetic retinopathy, i.e. stages 1 to 3 above, more preferably stage 1 and 2 above, and still more preferably stage 1 above or as a preventative therapy for patients having type 1 or type 2 diabetes who are at risk of developing diabetic eye disease, that occur before the release of substantial levels of growth factors that trigger the proliferation of new blood vessel in stages 4 and/or 3 of proliferative diabetic retinopathy.

Diabetic macular edema (DME) is the build-up of fluid (edema) in a region of the retina called the macula. The macula is important for the sharp, straight-ahead vision that is used for reading, recognizing faces, and driving. DME is the most common cause of vision loss among people with diabetic retinopathy. About half of all people with diabetic retinopathy will develop DME. Although it is more likely to occur as diabetic retinopathy worsens, DME can happen at any stage of the disease.

The diabetic patients who are at risk of diabetic eye disease include those with all types of diabetes (type 1, type 2, and gestational). The risk of developing diabetic eye disease increases the longer a person has diabetes. By way of example, between 40 and 45 percent of Americans diagnosed with diabetes have some stage of diabetic retinopathy, although only about half are aware of it. Women who develop or have diabetes during pregnancy may have rapid onset or worsening of diabetic retinopathy. Accordingly, the present invention may be used for the treatment of all of these patient types.

In addition, the medical uses and methods of the present invention may be employed for the preventative use in patients being brought into glycaemic control. In such treatment, when a patient with chronically high blood glucose levels is brought into glycaemic control, the eye tissues may have become used to the high glucose availability and become stressed as normal glucose levels are achieved. Accordingly, the present invention may be used to as a protective treatment as patients are being brought into glycaemic control.

These patients are at risk of experiencing worsening of diabetic retinopathy and could be protected as blood glucose is being brought under control.

The early stages of diabetic retinopathy usually have no symptoms. The disease often progresses unnoticed until it affects vision. Bleeding from abnormal retinal blood vessels can cause the appearance of "floating" spots. These spots sometimes clear on their own. But without prompt treatment, bleeding often recurs, increasing the risk of permanent vision loss. If DME occurs, it can cause blurred vision.

Diabetic retinopathy and DME may be detected during a comprehensive dilated eye examination that may include visual acuity testing (the use of an eye chart test measures a person's ability to see at various distances), tonometry (the measurement of pressure inside the eye, pupil dilation (in which drops placed on the eye's surface dilate (widen) the pupil, allowing a physician to examine the retina and optic nerve) and/or optical coherence tomography (OCT), a technique similar to ultrasound that uses light waves instead of sound waves to capture images of tissues inside the body. OCT provides detailed images of tissues that can be penetrated by light, such as the eye. A comprehensive dilated eye examination also allows the doctor to check the retina for changes to blood vessels, leaking blood vessels or warning signs of leaky blood vessels, such as fatty deposits, swelling of the macula (DME), changes in the lens and/or damage to nerve tissue. In cases where vascular leakage DME or severe diabetic retinopathy is suspected, a fluorescein angiogram may be used to look for damaged or leaky blood vessels. In this test, a fluorescent dye is injected into the bloodstream, often into an arm vein. Pictures of the retinal blood vessels are taken as the dye reaches the eye. There is a close translational link between the vascular leakage data we have generated in rats and this same method may be used to diagnose vascular leakage in humans.

Various routes of administration may be employed in connection with the methodology of the present invention, including, but not limited to, intraocular injection, systemic administration, oral administration, nasal spray, eye drops, or contact lenses.

In this connection, attainment of a concentration of the administered compound (or pharmaceutically acceptable salt or hydrate thereof) in the plasma of the subject in the range of from 50 nM to 5 µM may be desirable. The in vitro studies provided herein showed that an optimal effect was observed when concentrations of 50-100 nM of the GJIC modulator compounds were reached in the microenvironment of the retinal vessels. By way of example, this may be achieved when a plasma concentration of 50-100 nM was targeted by osmotic pump, or by local injection into the eye targeting a higher concentration in corpus vitreum, allowing for a concentration gradient towards the retinal vessels.

These data teach that effective doses to be administered to reach 50-100 nM in the microenvironment of the retinal tissues.

Compounds Suited for Use in Accordance with the Invention

An example of a compound well suited for use in accordance with the present invention is 1-(2-aminoacetyl)-4-benzoylamino-pyrrolidine-2-carboxylic acid, such as the (2S,4R) diastereomer thereof [i.e. (2S,4R)-1-(2-aminoacetyl)-4-benzoylamino-pyrrolidine-2-carboxylic acid], or a pharmaceutically acceptable salt or hydrate thereof. An example of an alternative name for this compound is (2S,4R)-1-(2-aminoacetyl)-4-benzamidopyrrolidine-2-carboxylic acid.

Other diastereomers of the latter compound (i.e. the 2S4S, 2R4R, 2S4R or 2R4S diastereomers) may also be value for use in the context of the present invention.

Another compound (peptide) suited for use in the present invention is Ac-DTyr-DPro-DHyp-Gly-DAla-Gly-NH$_2$ (vide supra).

Particular forms of these compounds may also be referred to as danegaptide and rotigaptide, respectively.

Pharmaceutically acceptable salt of danegaptide include danegaptide hydrochloride.

In addition to the compounds recited above, further compounds that may be suitable for use in the context of the invention include certain other GJIC modulating compounds, such as the antiarrhythmic peptides AAP (Aonuma et al., *Chem. Pharm. Bull.* (*Tokyo*), 28, 3332-3339 (1980)), AAP10 (Dhein et al., *Naunyn Schmiedebergs Arch Pharmacol.*, 350, 174-184 (1994); Muller et al., *Eur. J. Pharmacol.*, 327, 65-72 (1997)), HP5 (disclosed in U.S. Pat. No. 4,775,743) and other antiarrhythmic peptides as disclosed in WO 02/077017 or WO 2007/078990.

It will be appreciated that the compounds described herein may be used in combination. For example, more than one GJIC modulator compound may be administered in the methods described herein, either concurrently or sequentially.

Pharmaceutically Acceptable Salts

Pharmaceutically acceptable salts of compounds suited for use in accordance with the invention having an acidic moiety can be formed using organic or inorganic bases.

Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di- or trihydroxy lower alkylamine (e.g., mono-, di- or triethanolamine). Internal salts also can be formed. When a compound suited for use in accordance with the invention contains a basic moiety (as in the case of, e.g., 1-(2-aminoacetyl)-4-benzoylamino-pyrrolidine-2-carboxylic acid and the recited diastereomers thereof), salts may be formed using organic or inorganic acids. For example, salts can be formed from the following acids: acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic or camphorsulfonic. Other known pharmaceutically acceptable acids may also be employed. As already mentioned (vide supra), a preferred salt form of the (2S,4R) diastereomer of 1-(2-aminoacetyl)-4-benzoylamino-pyrrolidine-2-carboxylic acid is the hydrochloride monohydrate.

The present teachings may also extend to the use of prodrugs of the compounds disclosed herein as being suited for use in accordance with the present invention. As used herein, "prodrug" refers to a moiety that produces, generates or releases a compound of one of the disclosed types when administered to a mammalian subject, notably a human subject. Prodrugs can be prepared by modifying functional groups present in the compounds in such a way that the modifications are cleaved, either by routine manipulation or in vivo, from the parent compounds. Examples of prodrugs include compounds as disclosed herein that contain one or more molecular moieties appended (bonded) to a hydroxy, amino, sulfhydryl or carboxy group of the compound, and that when administered to a subject to be treated are cleaved in vivo to form the free hydroxy, amino, sulfhydryl or carboxy group, respectively. Examples of prodrugs include, but are not limited to, acetate, formate and benzoate derivatives of alcohol and amine functional groups in the compounds disclosed herein for use in accordance with the invention. Examples of preferred prodrugs include oxazolidinone or imidazolidinone prodrugs. Ester prodrugs may be formed with lower alcohols, such as 01-6 alcohols. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987.

Pharmaceutical Compositions

Compounds, or pharmaceutically acceptable salts or hydrates thereof, employed in accordance with the present invention may be administered in the form of appropriate pharmaceutical compositions, which can be administered via any acceptable method known in the art, either singly or in combination.

Pharmaceutical compositions of relevance in the present context may comprise a compound as disclosed herein for use in accordance with the invention in admixture with one or more pharmaceutically acceptable carriers, diluents, vehicles or excipients. In general, the pharmaceutical compositions used in accordance with the present invention may be adapted for administration of the compound in eye drops, contact lenses, nasal spray, intravitreally or systemically, e.g. by administration in the form of tablets or capsules.

Useful formulations may include formulations that provide sustained release of the compounds of the present teachings. These may be particularly useful for subsequent administration (after the first administration). The compositions are preferably in the form of liquid formulations, and methods for their preparation are generally described in "Remington's Pharmaceutical Sciences", 17th Ed., Alfonso R. Gennaro (Ed.), Mark Publishing Company, Easton, Pa., U.S.A., 1985. Such compositions generally contain an effective amount of the one or more active compounds of the present teachings, together with a suitable carrier in order to provide the dosage in a form compatible with the route of administration selected. Preferably, the carrier is in the form of a vehicle, a diluent, a buffering agent, a tonicity adjusting agent, a preservative and/or a stabilizer. The excipients constituting the carrier must be compatible with the active pharmaceutical ingredient(s) and are preferably capable of stabilizing the compounds without being deleterious to the subject being treated.

A form of repository or sustained-release formulation can be used so that therapeutically effective amounts of the preparation are delivered into the bloodstream over many hours or days following administration of the compound or composition, e.g., by transdermal injection or deposition. Formulations suitable for sustained release may comprise biodegradable polymers, such as L-lactic acid, D-lactic acid, DL-lactic acid, glycolide, glycolic acid, and isomers thereof. Similarly, the carrier or diluent can include any sustained release material known in the art, such as glyceryl monostearate or glyceryl distearate, alone or mixed with a wax.

Other sustained release formulations can include, but are not limited to, formulations that include at least one of the compounds disclosed herein combined with liposomes, microspheres, emulsions or micelles and liquid stabilizers.

The doses the compounds and compositions of the present invention required for the desired therapeutic effects will depend upon on the potency of the compound, the particular composition, used and the route of administration selected. The compounds will typically be administered in the range of about 0.001 g to 10 g per patient per day. For example, the compounds can be administered in the range from about 1 mg to about 1000 mg per patient per day, from about 10 mg to about 100 mg per patient per day, or about 50 mg per patient per day.

Administration of a compound (or pharmaceutical salt or hydrate thereof) in accordance with the invention may be conducted in a single unit dosage form (e.g. in the form of a bolus) or as a continuous therapy in the form of multiple doses over time. Alternatively, continuous infusion systems or slow release depot formulations may be employed. Two or more compounds for use in accordance with the invention (or pharmaceutical compositions thereof) may be co-administered simultaneously or sequentially in any order. In addition, the compounds and compositions may be administered in a similar manner for prophylactic purposes, for example if a diabetic patient deemed to be at risk of developing diabetic retinopathy or diabetic macular edema. Ultimately, the best dosing regimen will be decided by the attending physician for each patient individually.

Therapeutic Uses

Conditions which may be treated or prevented in accordance with the present invention using compounds as specified herein include diabetic eye diseases, such as diabetic retinopathy (and particular early stage diabetic retinopathy) and diabetic macular edema, especially in a human subject.

According to the invention, one or more of the compounds, or pharmaceutically acceptable salts or hydrates thereof (e.g. in the form of an appropriate pharmaceutical composition), may be administered to an individual in need thereof in a therapeutically effective amount.

As used herein, "a therapeutically effective amount" refers to an amount that is capable of reducing the symptoms of a given cerebrovascular condition or pathology, and preferably which is capable of partly or wholly normalizing physiological responses in a subject with the condition or pathology. Reduction of symptoms or normalization of physiological responses can be determined using methods known in the art and can vary with a given condition or pathology. The effective amount will be determined by the skilled person taking into account such factors as potency of the drug, age and constitution of the patient, body weight, pharmacokinetic profile of the drug, and in general the drug will be prescribed for each patient or group of patients.

The effective amount of the compound can be at least about 10 µg/kg body weight/day, such as at least about 100 µg/kg body weight/day, at least about 300 µg/body weight/day, and at least about 1000 µg/kg body weight/day. On the other hand, the effective amount of the compound or dimer can be at most about 100 mg/kg body weight/day, such as at most about 50 mg/kg body weight/day and at most about 10 mg/kg body weight/day. It is expected that the effective amount of the compound will be about 100 µg/kg body weight/day, about 300 µg/kg body weight/day or about 1000 µg/kg body weight.

The experiments provided in the in vitro system described herein dose finding as performed in the in vitro system (cell coupling assay/SLDT) show that a concentration of 50-100 nM is optimal in the microenvironment and the in vivo pilot study showed that 100 nM injections were better than 200 nM injections.

Experimental Examples

GJIC Modulator Compounds

Compounds (peptides) for use in accordance with the present invention may suitably be synthesized by means of solid-phase or solution-phase synthesis. In this context, reference may be made, for example, to Fields et al., "Principles and practice of solid-phase peptide synthesis", Synthetic Peptides (2002, 2nd Edition).

With regard to the preparation of 1-(2-aminoacetyl)-4-benzoylamino-pyrrolidine-2-carboxylic acid, such as the (2S,4R) diastereomer thereof, suitable methods of synthesis and purification thereof are described in WO2007/078990, in which the (2S,4R) isomer is denoted "Compound 2" (WO2007/078990 is incorporated by reference in its entirety).

An example of a useful salt form of the (2S,4R) diastereomer is the hydrochloride monohydrate, the preparation of which is described in WO 2008/079266, and which is also referred to in the present description as Compound X (WO 2008/079266 is incorporated by reference in its entirety).

With regard to Ac-DTyr-DPro-DHyp-Gly-DAla-Gly-NH$_2$, the solid-phase synthesis and purification thereof are described in WO01/62775 (in which the compound is denoted "Compound 2"). WO01/62775 is incorporated by reference in its entirety.

Animals

All animal studies were performed according to the ARVO Statement for the Use of Animals in Ophthalmic and Vision Research. In the pilot study to determine the optimal concentration of danegaptide, twelve Sprague-Dawley male rats, each weighing 200 g, were used. Nine of the twelve rats were injected intraperitoneally with streptozotocin (STZ) (55 mg/kg body weight) to induce diabetes for 6 weeks. The remaining 3 animals served as non-diabetic controls. After 6 weeks of diabetes, the animals were killed and retinas were isolated. In the follow-up study to determine the effect of 1000 nM danegaptide on the number of AC and PL, thirty-six Sprague-Dawley male rats, each weighing 200 g, were used. Thirty of the thirty-six rats were injected with STZ to induce diabetes for 15 weeks. The remaining six animals served as non-diabetic controls. After 15 weeks of diabetes, the animals were killed and retinas were isolated. The glucose concentration in blood and urine were checked after 2 or 3 days after STZ injection to confirm diabetes status in the animals. Blood glucose levels were measured in each animal 2-3 times weekly and at the time of death. The diabetic group represented rats with blood glucose levels of >350 mg/dL. The diabetic rats received NPH insulin injection as needed to maintain blood glucose levels.

Retinal Trypsin Digestion

The enucleated eyes were placed in 10% formalin for at least 24 hrs. The eyes were then cut in half with a razor blade, and the retinas were isolated and placed into 0.5M glycine for 24-48 hrs. RTD was performed as described in Kuwabara & Cogan (Studies of retinal vascular patterns. I. Normal architecture. Archives of ophthalmology 1960; 64:904-911). Each retina went through a series of washes with 3% trypsin, and the non-vascular mass of the retina was removed. The retinal capillary network was then isolated and mounted onto a silane-coated slide.

Assessment of Acellular Capillaries & Pericyte Loss

RTDs were stained with periodic acid-Schiff and hematoxylin as described in Bobbie et al. (Reduced connexin 43 expression and its effect on the development of vascular lesions in retinas of diabetic mice. Investigative ophthalmology & visual science 2010; 51:3758-3763). Ten representative fields were imaged using a digital camera attached to a microscope and the images were analyzed for AC and PL. Apoptotic pericytes were identified as PL based on prominent histological characteristics, including basement membrane protrusion as empty shell. Capillaries devoid of both pericytes and endothelial cells were considered as AC.

Results

Danegaptide Preserves GJIC and Reduces Apoptosis in Rat Retinal Endothelial Cells Rat retinal endothelial cells (RRECs) were grown for 3, 5, and 7 days in normal (N; 5 mM) or HG (30 mM) medium; in parallel, cells grown in HG medium were exposed for 3, 5, and 7 days to 100 nM Danegaptide (DG), an AAP10 analogue, which stabilizes Cx43 mediated cell coupling. In addition, cells grown in N medium were treated with a Cx43 blocker (negative control) which inhibits GJ coupling, or a positive control AAP10, protecting GJIC. To determine GJIC, scrape load dye transfer (SLDT) assay was performed at the three time points. Similarly, cells were assessed for apoptosis and cell monolayer permeability by differential dye staining assay and in vitro permeability assay, respectively.

RRECs treated with danegaptide showed preserved GJIC, decreased cell death, and reduced cell monolayer permeability. SLDT assay indicated that cells grown under HG conditions and exposed to danegaptide for 3, 5, and 7 days preserved GJIC. Similarly, danegaptide rescued cells from HG-induced apoptosis at all three time points. Additionally, cell monolayer permeability was significantly decreased by day 5. When cells grown in N medium were exposed to control AAP10, no changes in apoptosis or permeability were noted. Cells exposed to Cx43 blocker which decreased cell coupling showed excess apoptosis and cell monolayer permeability.

These findings suggest that prevention of HG-mediated compromised cell-cell coupling may be a useful strategy for inhibiting apoptosis and excess vascular permeability associated with diabetic retinopathy.

Danegaptide Prevents the Development of Acellular Capillaries (AC) and Pericyte Loss (PL)

Figure 1:
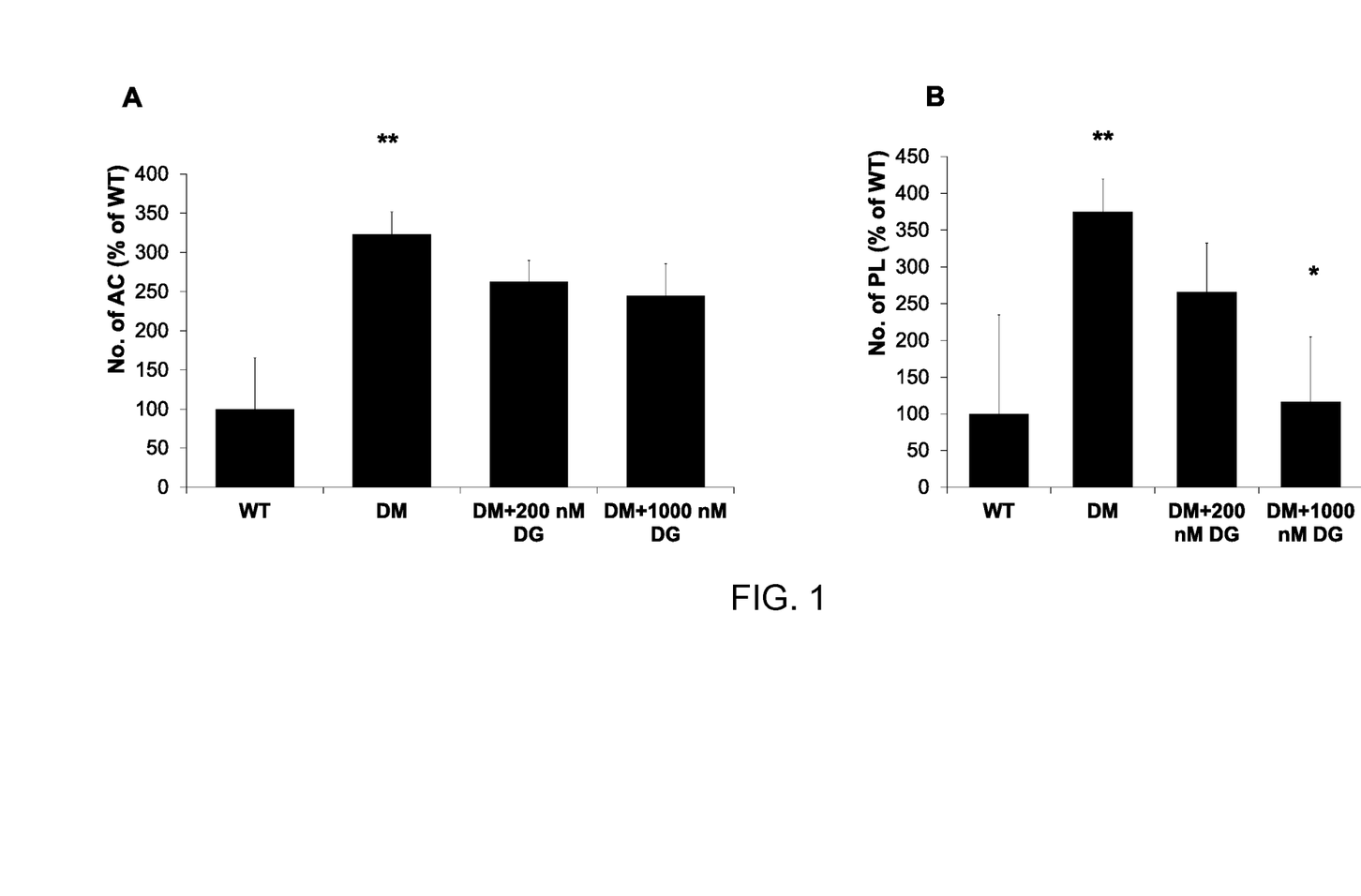
FIG. 1. Effect of 200 or 1000 nM danegaptide (DG) intravitreal injections against AC and PL development in diabetic rat eyes. The numbers of (A) AC and (B) PL were significantly increased in diabetic rat retinas compared to those of non-diabetic rat retinas (**=p<0.01). Intravitreal injection of 1000 nM danegaptide in diabetic rat retinas significantly reduced the number of PL compared to that of untreated diabetic rat retinas (*=p<0.05). The number of AC was decreased in the danegaptide treated groups but fell short of statistical significance possibly due to low number of animals (n=3).
Figure 2:
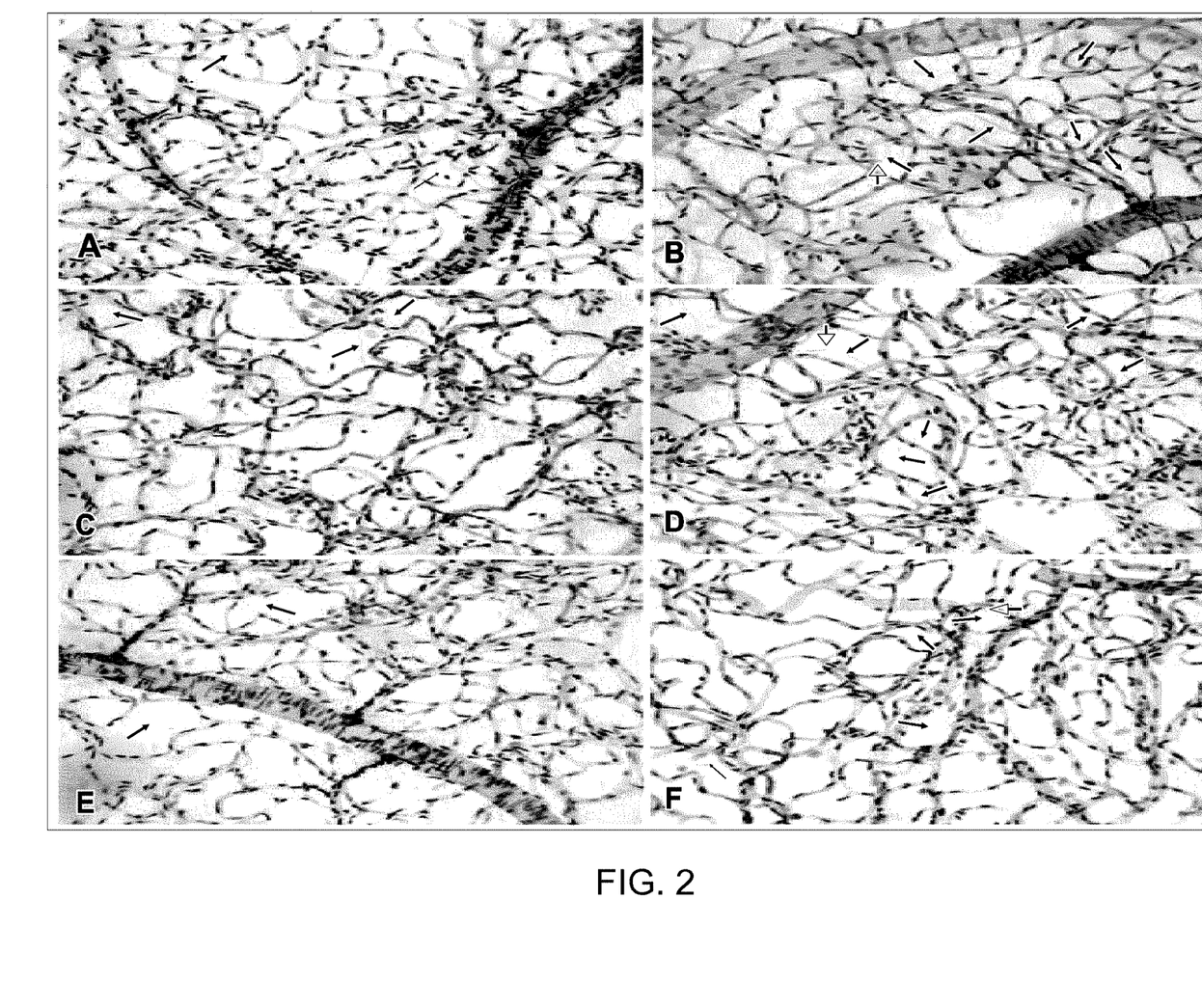

The results shown in FIGS. 1 and 2 demonstrate that administration of danegaptide, a Cx43 gap junction coupler, prevents the development of AC and PL in diabetic rat retinas. The improved cell-cell coupling promoted by the GJIC modulator compounds, via intravitreal injection or systemic delivery of danegaptide, protected against retinal vascular cell death in diabetic rat retinas.

The findings from this study suggest that administration of a gap junction coupler is protective against retinal vascular cell death in the retina. Moreover, results indicate that reduced cell-cell coupling and compromised GJIC activity in the diabetic retinas contribute, at least in part, to increased retinal vascular cell death as observed in diabetic retinopathy. The results in the present application therefore show that improving cell-cell coupling could be a used as strategy in treating or preventing retinal vascular cell loss associated with the pathogenesis of diabetic retinopathy or diabetic macular edema.

GJIC Modulator Compounds Protect Against Retinal Cell Death

In diabetic retinopathy (DR), cell-cell coupling appears to be compromised, leading to retinal vascular cell death and the development of retinal vascular lesions. This study is evaluated whether administration of a gap junction modulator is protective against retinal vascular cell death in the retinas of diabetic rats.

To determine the optimal concentration of danegaptide (DG), a Cx43 gap junction coupler, two concentrations (200 nM or 1000 nM) were tested via intravitreal injections in streptozotocin (STZ)-induced diabetic rats. Diabetes was induced via STZ for 6 weeks and at the end of the study, eyes were enucleated, and retinas subjected to retinal trypsin digestion (RTD) for isolation of capillary networks and stained with Hematoxylin and Periodic Acid Schiff's (PAS) reagent to analyze the number of acellular capillaries (AC) and pericyte loss (PL). Based on this pilot study, 1000 nM danegaptide was injected intravitreally in the follow-up study to determine the effect of improved cell coupling on retinal vascular cell death. Additionally, danegaptide was administered systemically using osmotic pumps. The number of rats used in this study was at least 6 per group. Overall, rats were divided into 6 groups: wild type (WT) control rats, STZ-induced diabetic rats, diabetic rats intravitreally injected with danegaptide, diabetic rats intravitreally injected with water, diabetic rats systemically delivered with danegaptide, and diabetic rats systemically delivered with water. Diabetes was induced via STZ for 15 weeks and at the end of the study, retinas were isolated and subjected to RTD for analyses of AC and PL.

The retinal vasculature showed a significant decrease in the development of AC in diabetic rats treated either via intravitreal injections or systemically with danegaptide (134±28% of control, $p<0.01$ and 133±37% of control, $p<0.001$, respectively) compared to those of diabetic rats (296±26% of control, $p<0.001$). Likewise, retinal capillaries of diabetic rats treated intravitreally or systemically with danegaptide exhibited a significant decrease in the number of PL (112±62% of control, $p<0.01$ and 103±65% of control, $p<0.005$, respectively) compared to those of diabetic rats (335±40%, $p<0.005$). Findings from this study indicate that improved cell-cell coupling are protective against retinal vascular cell death associated with diabetic retinopathy.

Determination of the Therapeutic Potential of Danegaptide in Preventing Retinal Vascular Lesions in an Animal Model of Diabetic Retinopathy To determine if improvement in Cx43-mediated gap junction intercellular communication (GJIC) prevents retinal vascular cell death and excess retinal vascular permeability, danegaptide was administered intravitreally or via osmotic pumps in rats. 60 male Sprague Dawley rats were randomly assigned into six groups, each consisting of 10 rats: non-diabetic rats, diabetic rats, diabetic rats intravitreally injected with DG (1000 nM concentration), diabetic rats intravitreally injected with sterile water as vehicle, diabetic rats treated systemically with DG (70 mg/mL to achieve 100 nM plasma DG concentration) via osmotic pumps, and diabetic rats treated systemically via osmotic pump with sterile water as control. Diabetes was induced via STZ for 15 weeks and at the end of the study all animals were examined and subsequently sacrificed and their retinas were examined for (i) in vivo permeability (IVP), (ii) RTD, and (iii) optical coherence tomography (OCT) for analyses of vascular leakage, AC and PL, and retinal thickness, respectively.

In Vivo Permeability Data

Figure 3:
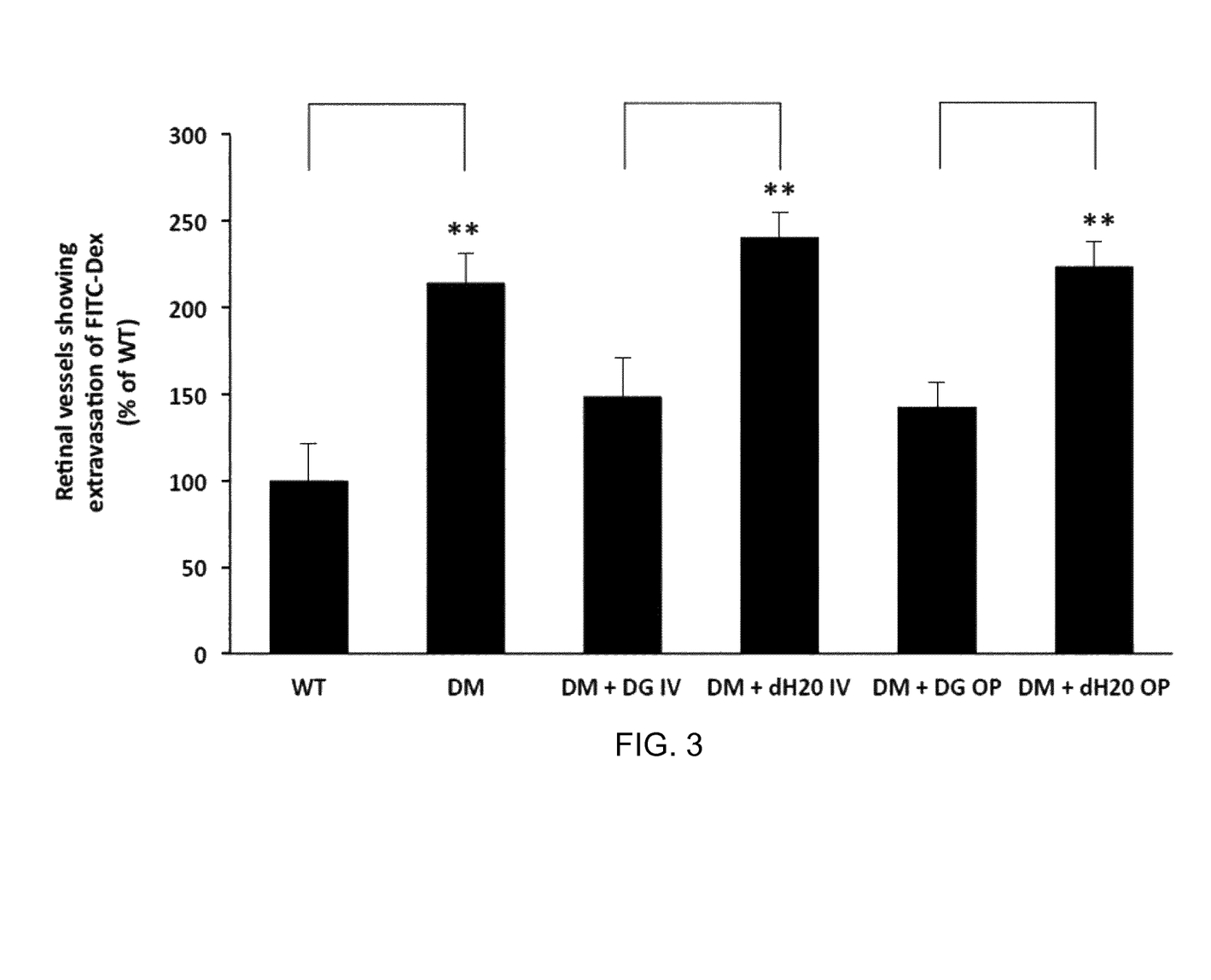
Figure 4:
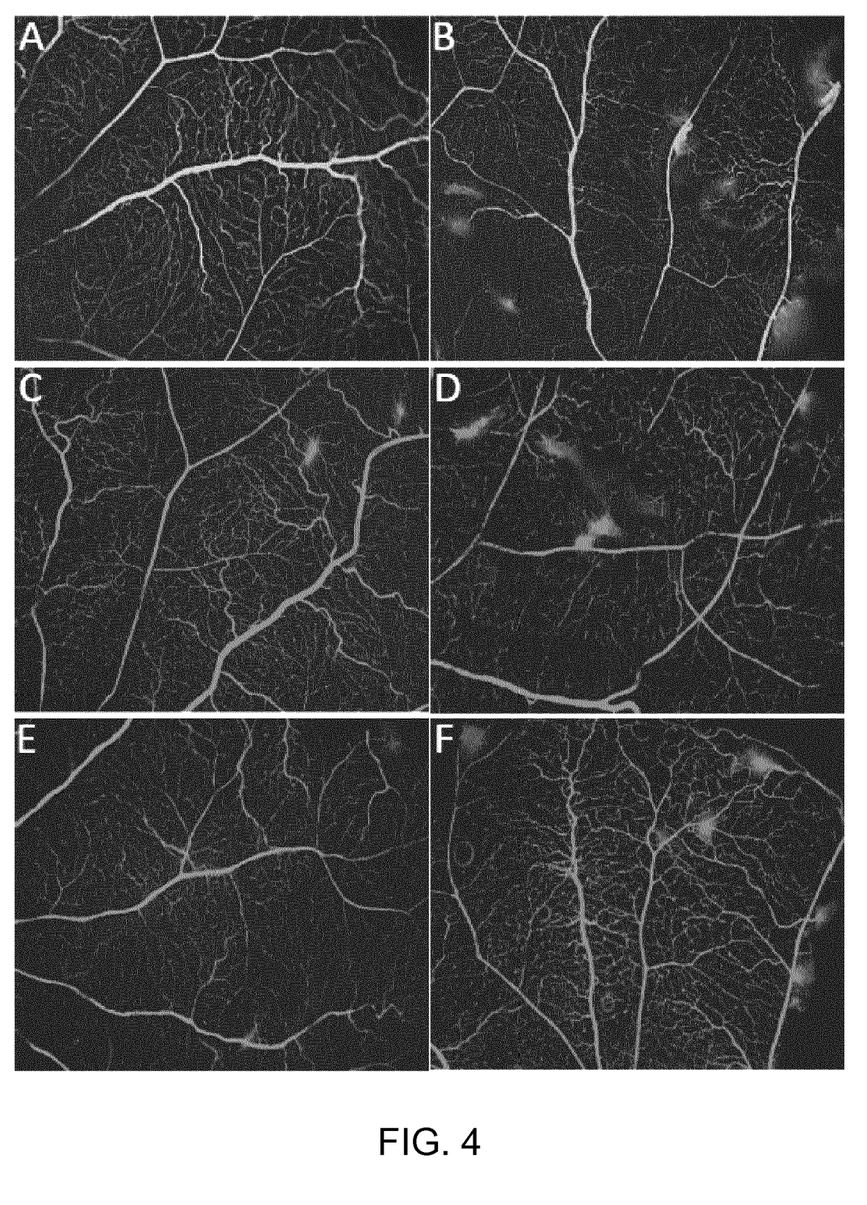

To determine the effect of improved cell-cell coupling on retinal vascular permeability under hyperglycemic stress, extravasation of FITC-dextran was assessed in the retinal capillaries following FITC-dextran tail vein injection performed shortly before animals were sacrificed. The retinal capillary networks of the diabetic rats exhibited increased vascular leakage compared to those of the non-diabetic rats (214±17% of control vs 100±22% of control, $p<0.001$). Importantly, retinal capillary networks of diabetic rats treated intravitreally with DG exhibited a significant decrease in vascular leakage compared to those of diabetic rats treated intravitreally with water as control (149±22% of control vs 241±14% of control, $p<0.001$) (FIGS. 3, 4). Similarly, retinal capillary networks of diabetic rats treated systemically with DG exhibited a significant decrease in vascular leakage compared to those of diabetic rats treated systemically with water as control (143±14% of control vs 224±14% of control, $p<0.001$) (FIGS. 3, 4). Moreover, there was no significant difference in vascular leakage between diabetic rats treated with intravitreal injections of DG and diabetic rats treated systemically with DG.

Transcriptomic Effects of Danegaptide in an In Vitro Diabetic Retinopathy Model

The transcriptomic effects of danegaptide in an in vitro diabetic retinopathy model were investigated to 1) reveal transcriptomic changes in diabetic-like conditions with or without danegaptide and 2) associate functional effects previously observed to transcriptomic modifications and 3) identify pathways involved in danegaptide effects on relevant cells under diabetes-like conditions. Primary retinal endothelial cells from rats were plated for in vitro experiments under four experiments conditions, Normal Glucose medium (NG), High Glucose medium (HG), High Glucose medium+Danegaptide 100 nM (HG_DG100) and High Glucose medium+Danegaptide 1000 nM (HG_DG1000). The samples were assessed at four time points (4 hours after plating, 1 day after plating, 3 days after plating and 5 days after plating).

Figure 5:
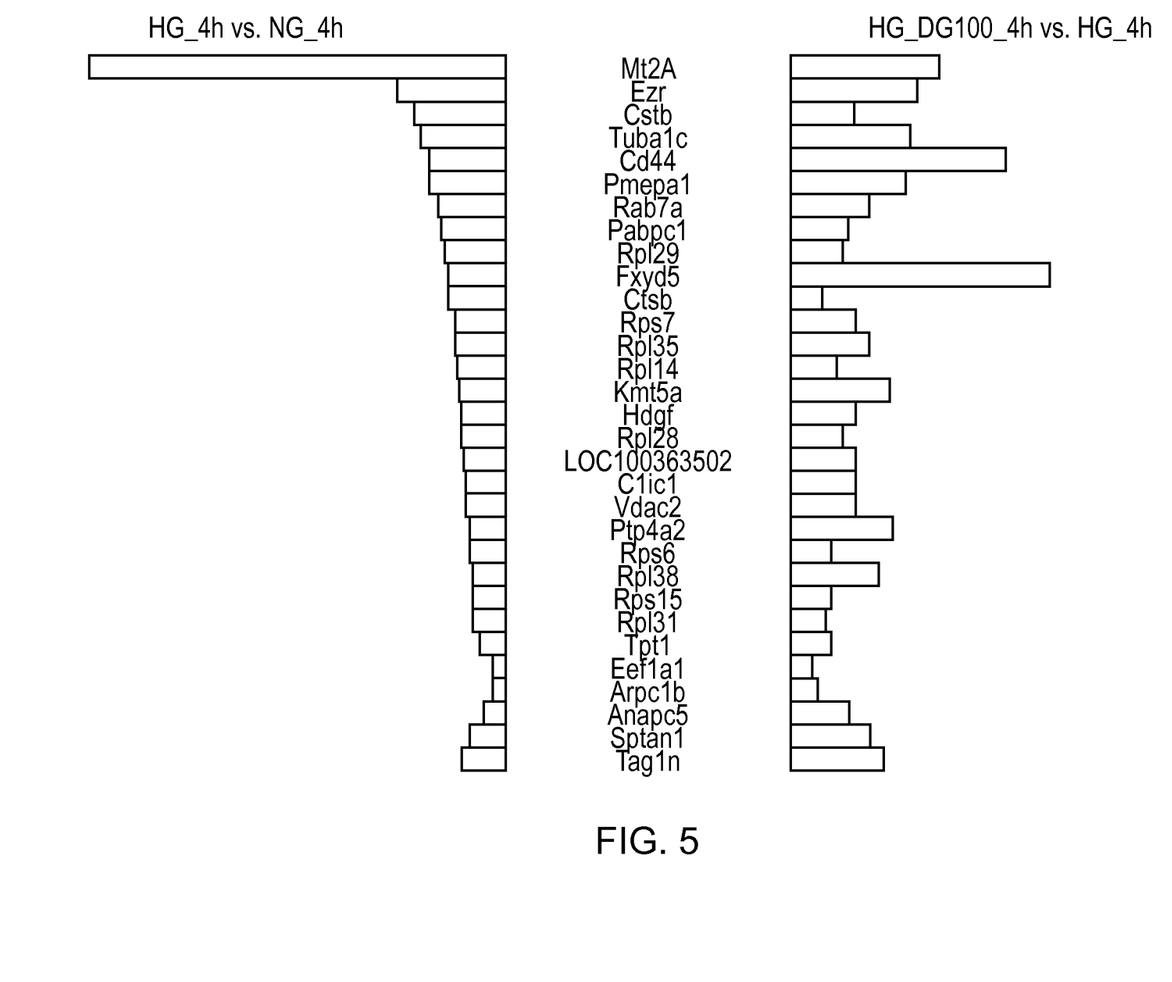
FIG. 5. Danegaptide reverse some changes in genes expression at 4 h with NOISeqBIO. Dark grey bars refer to down-regulation of transcripts. Light grey bars refer to up-regulation of transcripts. Thresholds: Padj<0.05.
Figure 6:
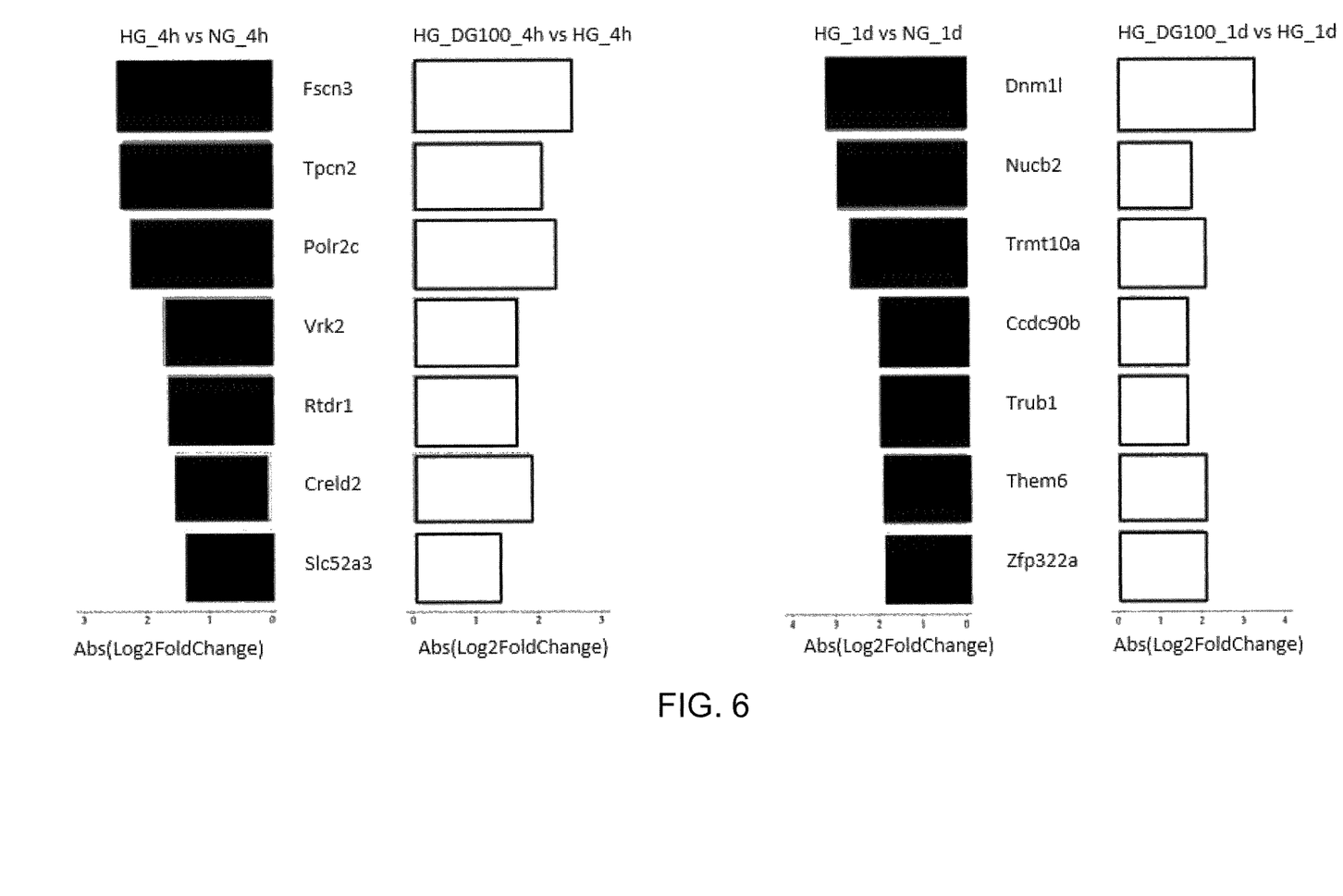
FIG. 6: Danegaptide reverse some changes in genes expression at 4 h (left) and 1 d (right) with DESeq2. Black bars refer to down-regulated genes. White bars refer to up-regulated genes. Thresholds: Padj<0.05

These experiments showed that danegaptide induces changes in gene expression in HG cells and for some genes reverses changes induced by HG as compared to NG conditions. The experiments also confirmed that danegaptide induces changes in gene expression in cells exposed to high glucose and that danegaptide reverses expression of some genes differentially expressed in high glucose conditions compared to normal glucose conditions (FIGS. 5 and 6). These figures describe transcriptomal changes at 4 hours and 1 day, using two different method of analysis (DESeq2 and NOISeqBIO). The data shows that the pattern of transcriptomal changes alters with time. In particular, the experiments found that Fscn3 (an actin-bundling protein downregulated in HG versus NG and reverse by danegaptide) is commonly downregulated in cells exposed to high glucose, associated with myosins and Cadherins, and implicated in GlcNac process altered in diabetic retinopathy. Also Tpcn2, a gene that may play a role in human diabetes is downregulated in HG versus NG and reversed by danegaptide at 4 h and interact with ESR1 which is involved in Sp3-dependent diabetic retinopathy pathways. Several transcripts like Dnm1l, Nucb2, Trmt10a were all down-regulated at day 1 under HG conditions and danegaptide generally increased the expression of these transcripts indicating possible protective effects from HG stress (FIG. 6). At 1 d, the experiments found that Cacybp gene is downregulated in HG versus NG and reversed by danegaptide. This gene interacts in functions with SIN3A, a major upstream regulator of the hyperglycemia-induced Ang2 pathway leading to diabetic retinopathy.

All publications, patent and patent applications cited herein or filed with this application, including references filed as part of an Information Disclosure Statement are incorporated by reference in their entirety.

The invention claimed is:

1. A method of treating early stage diabetic eye disease or diabetic macular edema in a human subject, the method comprising administering to the human subject a therapeutically effective amount of the compound, or a pharmaceutically acceptable salt or hydrate thereof, wherein the compound is selected from the group consisting of:
   (2S,4R)-1-(2-aminoacetyl)-4-benzoylamino-pyrrolidine-2-carboxylic acid; and
   Ac-DTyr-DPro-DHyp-Gly-DAla-Gly-NH$_2$;
   or a pharmaceutically acceptable salt or hydrate thereof.

2. The method of treatment according to claim 1, wherein the compound is (2S,4R)-1-(2-aminoacetyl)-4-benzoylamino-pyrrolidine-2-carboxylic acid, or a pharmaceutically acceptable salt or hydrate thereof.

3. The method of treatment according to claim 1, wherein the method is for the prevention of early stage diabetic retinopathy or diabetic macular edema in a human subject.

4. The method of treatment according to claim 1, wherein the diabetic retinopathy is mild non-proliferative retinopathy or moderate non-proliferative retinopathy in a human subject.

5. The method of treatment according to claim 1, wherein the compound is for use in treating or preventing diabetic macular edema.

6. The method of treatment or prevention according to claim 1, wherein the compound is for preventative treatment of a patient with a chronically high blood glucose level as the patient is brought into glycaemic control.

7. The method of treatment according claim 1, wherein the compound inhibits pericyte loss in the retina.

8. The method of treatment according to claim 1, wherein the compound inhibits vascular leakage in the retina.

9. The method of treatment according to claim 1, wherein the compound inhibits apoptosis of retinal endothelial cells.

10. The method of treatment according to claim 1, wherein the patient has type 1 diabetes, type 2 diabetes or gestational diabetes.

11. The method of treatment according to claim 3, wherein the method prevents a progression of early stage diabetic retinopathy or diabetic macular edema in a human subject to mild non-proliferative retinopathy or moderate non-proliferative retinopathy.

12. The method of treatment according to claim 4, wherein the method prevents a progression of mild non-proliferative retinopathy or moderate non-proliferative retinopathy in a human subject to severe non-proliferative retinopathy.

* * * * *